United States Patent [19]
Golbs et al.

[11] Patent Number: 5,910,493
[45] Date of Patent: Jun. 8, 1999

[54] HORMONAL AGENT FOR SKIN TREATMENT

[75] Inventors: Siegfried Golbs, Leipzig; Michael Oettel, Jena; Michael Dittgen, Apolda; Thomas Graser, Erfurt; Christoph Luderschmidt, Munchenl, all of Germany

[73] Assignee: Jenapharm GmbH, Jena, Germany

[21] Appl. No.: 08/714,463

[22] Filed: Sep. 16, 1996

[30] Foreign Application Priority Data

Sep. 16, 1995 [DE] Germany ............... 195 34 209

[51] Int. Cl.$^6$ .................................. A61K 31/56
[52] U.S. Cl. ................ 514/170; 514/178; 514/182; 514/859; 514/864
[58] Field of Search .................... 514/170, 178, 514/182, 859, 864

[56] References Cited

PUBLICATIONS

"Purification of Androgen Receptors in Human Sebocytes and Hair", by M. Sawaya, The Society for Investigative Dermatology, Inc.

"Localization of androgen receptors in human skin by immunohistochemistry: implications for the hormonal regulation of hair growth, sebaceous glands and sweat glands", by R. Choudhry et al, in J. Endocr. 133, pp. 467 475, 1992.

Phytoestrogens—A Short Reveiw, by David C. Knight, John A. Eden, Royal Hospital for Women.

A Review of the Clinical Effects of Phytoestrogens, by David Knight, FRACOG and John A. Eden, FRACOG., vol. 87, No. 5, Part 2, May 1996.

*Primary Examiner*—Leonard Schenkman
*Attorney, Agent, or Firm*—Michael J. Striker

[57] ABSTRACT

The pharmaceutical composition, especially for treating skin with seborrhea, *Acne vulgaris* and androgonically conditioned alopecia, contains a hormonal agent including the gestogen, dienogest, or a combination of dienogest and an estrogen, as active ingredient. Methods for treatment of this type of skin condition include topical application of the composition including the dienogest which results in an outstanding sebosuppression, a drastic reduction of androstandiol glucuronide and a moderate competitive blockage of androgen receptor sites. Galenic formulations are described which limit and/or prevent the permeation of the active ingredient through the skin. The pharmaceutical preparation including the dienogest and conventional dermatologically acceptable carrier and auxiliary substances in the described galenic formulation advantageously provides a drastic reduction in androstandiol glucuronide and moderate androgen receptor blockage without passing through the skin barrier so that systemic effects including side reactions are substantially prevented.

16 Claims, 4 Drawing Sheets

Free Androstandiol Glucuronide in Serum

HORMONAL AGENT FOR SKIN TREATMENT

BACKGROUND OF THE INVENTION

The present invention relates to a hormonal agent or composition for skin treatment, especially seborrhea, *Acne vulgaris*, androgenically conditioned alopecia and androgenic symptoms of women.

In central Europe the incidence of hormonally conditioned skin diseases, such as acne, seborrhea and hirsutism, is estimated at 35 to 50%. These illnesses appear primarily in young men and women after puberty who are exposed to considerable suffering because of them (H. Hagen, et al, Klinische Erfassumg antiandrogener Effekte von Dienogest {Clinical Determination of antiandrogenic effects of dienogest}, pp. 223–230 in "Dienogest-Präklinik und Klinik eines neuen Gestagens", A. Teichmann, ed, Walter de Gruyter Verlag, Berlin, N.Y., 1995).

The sebaceous gland activity is considerably influenced by hormones. Testosterone and dihydrotestosterones are responsible for the sebocyte proliferation and sebogenesis and provide, as a result, the driving force for sebogenesis. An interaction with androgen receptors, which are localized in human skin (acne areas, such as the face, upper breast portions, the V-shaped region of the back and the outer sides of the upper arms), especially the sebaceous gland and sebaceous gland follicle, is, among other things, a prerequisite for this(R. Choudhry, et al, "Localization of androgen receptors in human skin by immunohistochemistry: implications for the hormonal regulation of hair growth, sebaceous gland and sweat glands", in J. Endocr. 133, pp. 467–475(1992); M. E. Sawaya, "Purification of androgen receptors in human sebocytes and hair", in J. Invest. Dermat. 98, pp. 92–96(1992).

Continuous sebum production increases in acne patients depending on the androgen secretions and the peripheral response of the end organs and reaches its highest value in *Acne conglobata*.

A hormonal agent or composition which is described in German Patent DE-PS 43 21 957 is used for acne therapy. This hormonal agent is a composition which is taken orally. Because of its systemic action undesirable effects and material accumulation occur in acne patients. Besides the hormonal treatment of acne it is also known to stimulate hair growth. In German Patent Document DE 36 15 396 a combination preparation comprising a hair tonic including cyproteron acetate in hair tonic is used as a combined preparation for treating the scalp skin and for promotion of hair growth.

The action of cyproteron acetate and chlormadinon acetate during therapeutic application is based on a centrally mediated antigonadotropic effect. Because of that an acne therapy and/or treatment of alopecia in humans is not possible with these active ingredients. Furthermore cyproteronic acetate and chlormadinon acetate causes a peripheral competitive androgen receptor blockage in acne of women (Ch. Luderschmidt, "Die Akne der Frau{The Acne of Women}" in Gynäkol. Prax., 19, pp. 479–488, 1995).

SUMMARY OF THE INVENTION

It is an object of the present invention to provide a pharmaceutical composition, especially for the treatment of acne, seborrhea or alopecia, in which the systemic effect of the hormonal agent acting as active ingredient is prevented and a direct peripheral effect is produced at the place of occurrence on the skin (seborrhea, acne areas, alopecia, androgenic symptoms of women) and which may be used in both women as well as men.

It is another object of the invention to still further limit and/or to hinder the permeation of the active ingredient through the skin by suitable galenic measures. Because of these measures the penetration of the skin by the active ingredient is promoted instead of hindered. However the permeation by the substances is controlled by the formulation so that the active material is not available or only slightly available systemically in order to avoid or minimize undesirable effects in the organism.

It is an additional object of the invention to provide a manufacturing or production process for the pharmaceutical composition in which the active ingredient is stable and prepared thermodynamically active so that, after it is applied to the skin, it penetrates the skin very rapidly and to a great extent, however slightly or only in a very much reduced extent by the most diverse penetration paths, e.g. transfollicularly, transglandularly and transepidermally. This process should further guarantee that the active ingredient does not come into contact with water, reactive solvents or surfactants or light for a long period of time.

Particularly it is an object of the present invention to include defatting or deoiling substances, like those described in German Patent Document DE 42 29 820, which promote the penetration of hormonal active ingredients in the skin, for a local, but nonsystemically effective, application. The use of defatting or deoiling substances should prevent or hinder the stimulation of the skin to overproduce oil or fat because of oil or fat removal.

The method of applying the pharmaceutical composition topically after it is prepared by the preparative methods according to the invention releases the active ingredient as fast as possible and as completely as possible, promotes its passage into the skin tissue while avoiding absorption and thus introduces no undesirable reciprocal action (interactions) with the biological tissue, as are known, for example, for certain solvents and surfactants.

According to the invention these objects are attained by a method of topical treatment of *Acne vulgaris*, seborrhea, androgonically conditioned alopecia and androgenic symptoms of women comprising the step of applying locally on the skin a pharmaceutical composition containing the antiandrogenically acting gestogen, dienogest, or a combination of dienogest and an estrogen, especially 17α-estradiol or estriol.

BRIEF DESCRIPTION OF THE DRAWING

The objects, features and advantages of the invention will now be explained in greater detail in the following description of preferred embodiments, with reference to the accompany drawing, in which.

DESCRIPTION OF THE PREFERRED EMBODIMENTS

Figure 1:
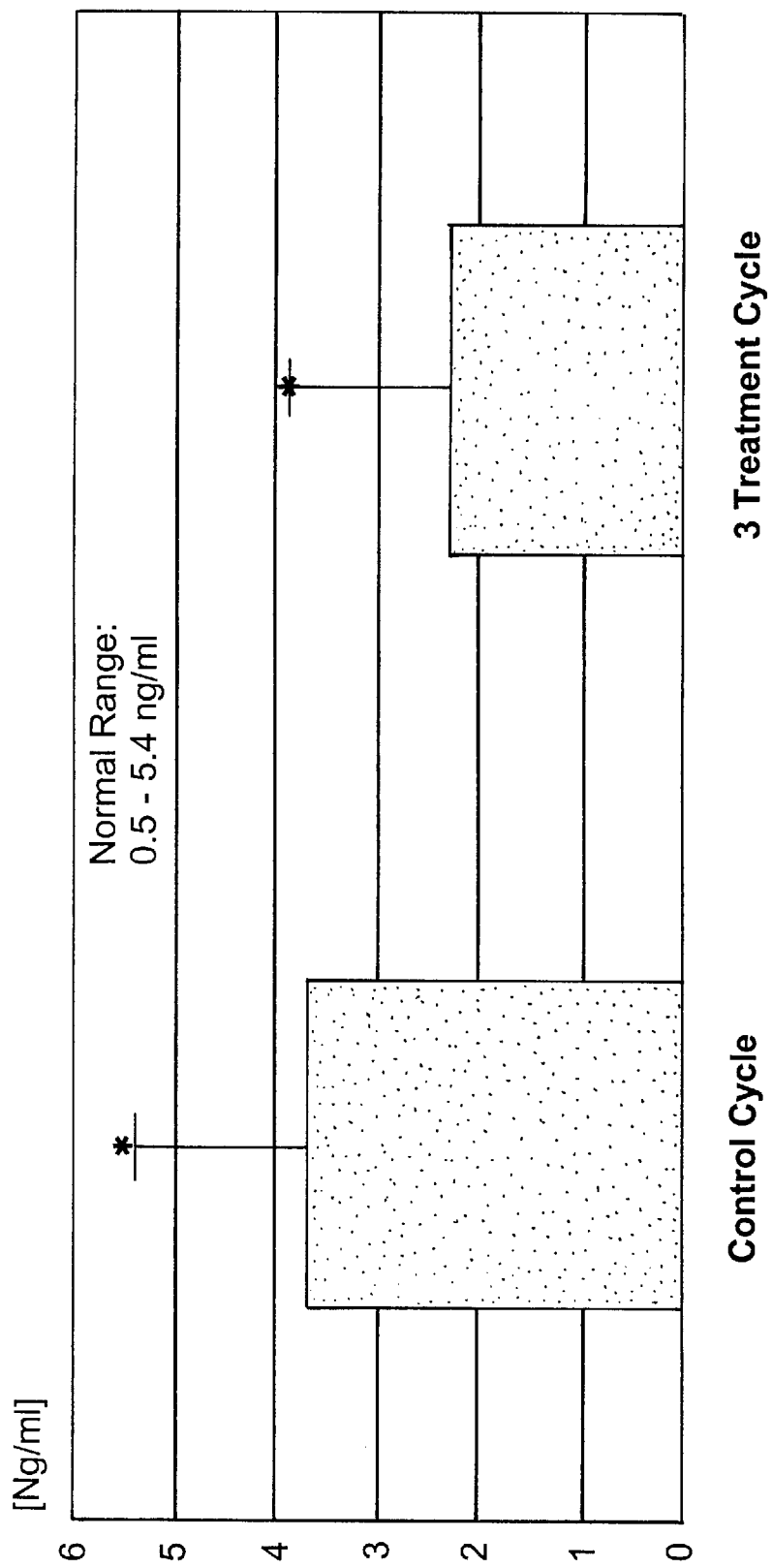
FIG. 1 is a bar graph illustration showing the drastic reduction in androstandiol glucuronide concentration in serum occurring after topical treatment using the pharmaceutical composition according to the invention.

The dienogest produces an outstanding sebosuppression when it is applied topically. Because of that, as shown in FIG. 1, appended hereinbelow, a drastic reduction of androstandiol glucuronide concentration in serum and a moderate competitive inhibition of androgen receptors occurs. Androstandiol glucuronide is regarded as a marker of the peripheral conversion of testosterone into dihydrotestosterone. It has been shown that dienogest acts at the level of a stronger antiandrogen such as cyproteron acetate in LNcaP cells in vitro. In combination with an estrogen, such as 17α-estradiol or estriol, the suppressive effects of the hormonal agent according to the invention are increased. At the beginning of the topical treatment particularly there is a direct action of the estrogen on sebogenesis to reduce the sebum influence. A definite reduction in sebaceous gland surface area has also been proven. Androgen receptors in the shrunken sebaceous gland may be detected only rarely or not at all. The acne improves after three to four weeks of treatment. The topical application of a combination of dienogest and an estrogen in a suitable galenic form is advantageous with significant acne.

In contrast to the two gestogens, cyproteron acetate and chlormadinon acetate, dienogest in the galenic preparation described in this patent, does not penetrate through the skin and acts directly on end organs. Because of this dienogest, also in combination with an estrogen, has the major advantage that it acts directly on skin end organs in topical application in male and female patients.

Figure 2:
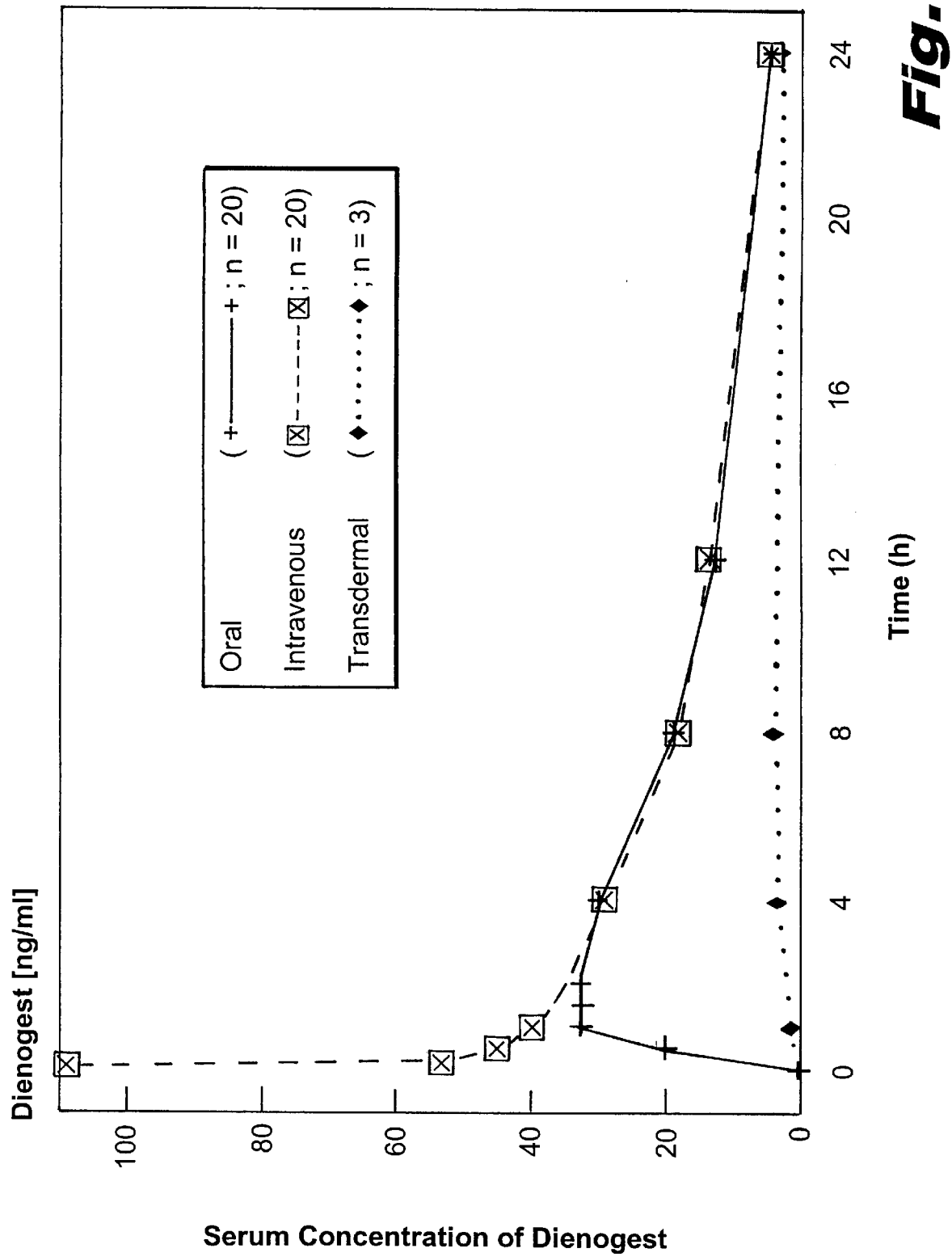
FIG. 2 is a graphical illustration of the relationship of serum concentration of dienogest and time when the dienogest is taken orally, intravenously or applied topically.

Concentration-time experimentally determined curves show that 10 mg of dienogest, delivered transdermally, in contrast to the results or oral and/or i.v. application (2 mg of dienogest), do not penetrate the skin barrier. The concentration-time curves illustrated in FIG. 2, described hereinbelow, clearly show that this is the situation. The dienogest concentration values in serum vary in the vicinity of predetermined limits (1 ng/ml) after transdermal distribution. A systemic effect of dienogest is not expected until its concentration in serum reaches 10 ng/ml.

A systemic action of dienogest is however prevented, since the active ingredient in the proposed galenic formulation does not penetrate the skin barrier and thus can not cause systemic effects. Because of that undesirable systemic side-effects, which, among other things, can occur on oral application, are prevented in this type of topical application. In the galenic preparation(salve, cream, lotion, facial tonic, hair tonic or hair balm) the gestogen, dienogest, is contained or present advantageously in an amount between 0.01 to 4 percent by weight in the preparation.

According to the invention the effective ingredient in the galenic preparation is present in a hydrophilic or deoiling foundation in a thermodynamic state suitable for the preparation. The effective ingredient is thus prepared so that it is distributed molecularly dispersed in the deoiling or hydrophilic foundation. In the case of a hydrophilic preparation (aqueous solution, hydrogel, lotion or O/W emulsion) it is sufficient that the gestogen is dissolved in ethanol or a similar vehicle and added in this form. In the case of the deoiling preparation (lipogel or a preparation containing at least one partly fatty or similar substance, e.g. a W/O emulsion) the active ingredient is combined with a hydrophilic component (H) and generally molecularly dispersed in it. Advantageously sugar or sugar-like substances, such as saccharose, lactose, mannitol, sugar alcohol, urea or other N-containing compounds can be used as the hydrophilic ingredient(H). On contact with skin liquids (e.g. sweat) the hydrophilic ingredient sees to it that the effective ingredient very rapidly goes into solution and penetrates the skin.

It has also proven to be advantageous to mix the solution of the active ingredient with a permeation promotor and/or a stabilizer. The permeation promotor additionally promotes the absorption of the active ingredient in the skin. A nitrogen-containing compound, e.g. an acid amide, an amine or an alkaloid, may be used as permeation promotor. Urea is particularly suitable as permeation promotor.

The stabilizer provides the active ingredient with a sufficient stability, especially in the case of the solution. The antioxidants known from basic principles, such as tocopherol, can be used as the stabilizer, however also complex formers, reducing agents and/or UV-absorbers may also be considered. The permeation of the effective ingredient by the skin is limited and/or hindered by the preparation according to the invention and a comparatively high availability of the active ingredient on the skin is provided. When the preparation according to the invention based on a deoiling foundation is used in addition the stimulation of oil overproduction is countered, since a certain controlled amount of oil required for reconstituting the skin is provided.

For example, oils(e.g. peanut oil and/or castor oil), waxes (e.g. bees wax, hard wax, fluid wax), hydrogels, ethanol, water, benzyl benzoate, isopropyl myristate, lecithin, glycerol, lanolin, boric acid, sodium tetraborate, lactic acid, viscous fluid paraffin, propylene glycol, deionized water or a mixture of these compounds can be used as the carrier/ auxiliary substances for the locally applied preparation including dienogest. With the help of this preparation the cutaneous pharmacological action of the antiandrogenically acting gestogen, dienogest, also in combination with an estrogen, the reduction of sebogenesis (estrogen effect) to sufficient extent in the skin is guaranteed. Because of that sebosuppression occurs, which leads to a reduction of sebaceous gland surface and elimination of comedones. A disadvantgeous action of the dienogest is not present because of the gelenic preparation. Damage to the treated skin (horny skin, hair follicules) does not occur.

Allergic and toxic reactions are not to be expected because of the active ingredient, the combination of the active ingredient with estrogen and also the additive and auxiliary materials.

Figure 3:
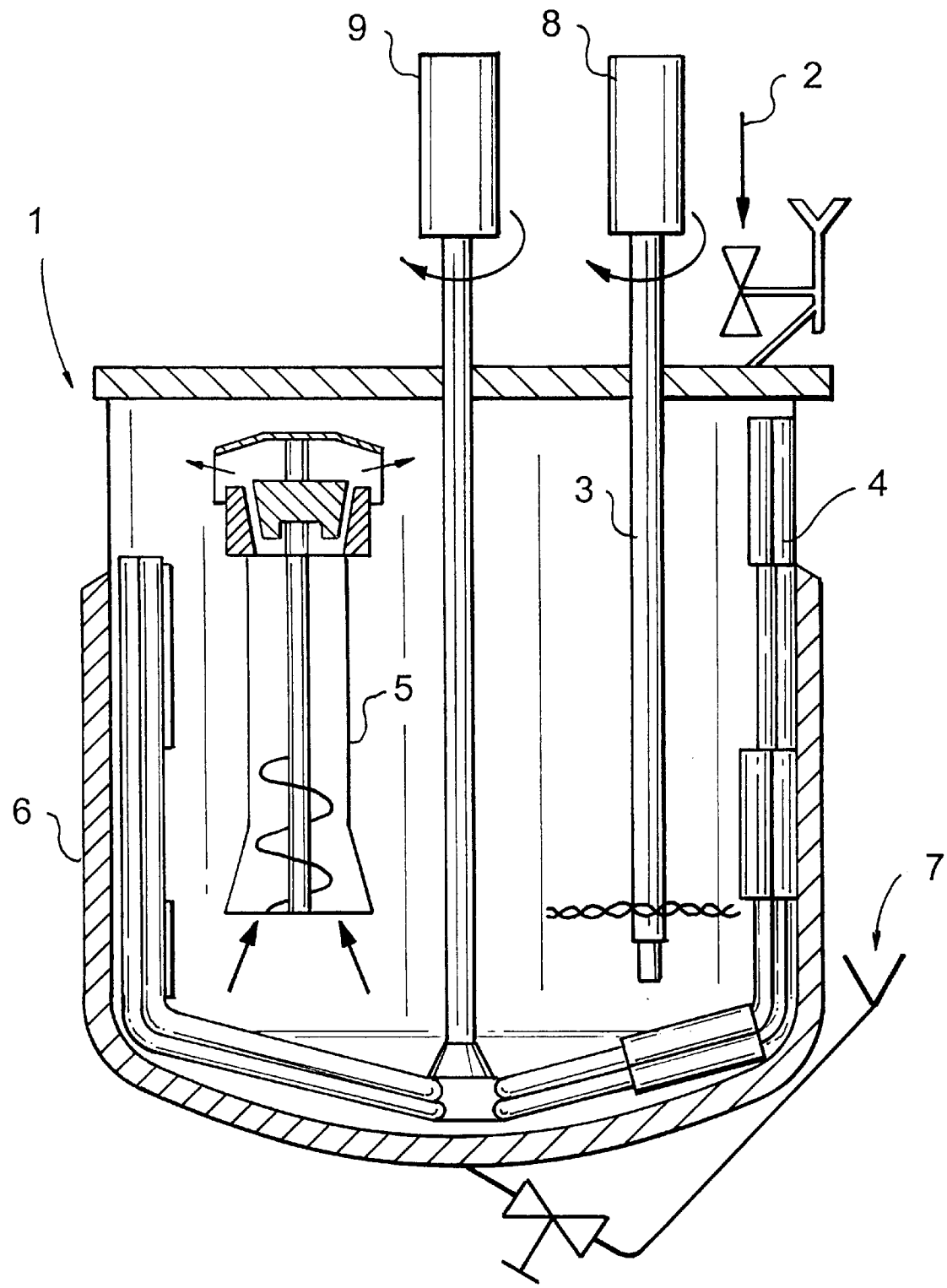
FIG. 3 is a cross-sectional view through a reaction vessel for production of the pharmaceutical composition according to the invention.

A closed system is suitable for making the pharmaceutical preparation according to the invention. The active ingredient, protected from light, is combined in a predetermined weight ratio with a permeation promotor and a stabilizer in the closed system and is in the same process at most briefly heated and can be dispersed with the aid of a high speed mixer in a lipophilic or hydrophilic vehicle. To make the pharmaceutical preparation according to the invention advantageously the apparatus shown in FIG. 3 is used, which comprises a closed vessel 1 which is equipped with a first stirring apparatus 3, a second stirring apparatus 5, a wiper apparatus 4 and laterally with a heatable or coolable jacket 6. The vessel 1 is provided with an upper filling connector pipe 2 and a lower filling connector pipe 7. Drive devices 8 and 9 are provided for the respective apparatuses 3 and 4.

The method of making the preparation according to the invention is now described for the pharmaceutical preparation with the gestogen, dienogest, as active ingredient. A mixture of conventional additive materials often used in dermatological compositions (see the example) is present in vessel 1. The additive materials are introduced in liquid or solid form through the upper filling connector pipe 2. The first slowly running stirring apparatus 3 is put into rotation by operating the drive device 8. At the same time a wiper apparatus 4 is activated so that a minimum amount of material adheres to the edges of the vessel 1. In a hydrophilic preparation the gestogen, dienogest, is introduced through the lower filling connector pipe 7 as a pure substance or dissolved in a hydrophilic vehicle. A permeation promotor and/or stabilizer is added jointly with the gestogen or after the active ingredient is completely dispersed in the mixture with the additive materials. After that, the entire mixture is homogenized with the help of the comparatively more rapidly running stirring apparatus 5. Depending on the rigidity of the mixture usually brief heating occurs. Usually however at the beginning of the homogenization a cooling must be performed.

The cooling interval is essential for the stabilization of the thermodynamic state of the gestogen in the preparation. The cooling and stirring speeds are decisive for the effectiveness of the gestogen in the resulting preparation with a given recipe and concentrations of homogenizer/stabilizer. Furthermore the stability of the gestogen in the preparation essentially depends on the temperatures existing during the making of the preparation. It has proven particularly advantageous when the temperature in the vessel and similarly the rotation speed of the stirring devices are regulated stepwise and are related in a definite manner to the heating/cooling rate of the jacket surrounding the vessel. Air or liquid (water) can flow through the jacket.

In the method of making the pharmaceutical preparation based on a deoiling foundation the pharmaceutically active ingredient is mixed in a separate vessel with a hydrophilic component or ingredient. This mixture is heated to at least partially melt it while excluding water, other solvents and/or surfactants and subsequently is dispersed with rapid cooling in a gas. The intermediate product arising therefrom is now added to another mixture of auxiliary materials commonly used in dermatological preparations which was prepared in an additional vessel and is dispersed uniformly in the galenic preparation. Either jointly with the active material or after the active material has been completely dispersed, a permeation promotor and/or stabilizer is added. The temperature is increased so that a creamy mixture is guaranteed. Besides a first stirring device with a comparatively lower rotation speed a second stirring device with a comparatively higher rotation speed is used as homogenizer. The temperature of the preparation is now continuously lowered. The cooling rate is advantageously about 1° C./min.

The making of a galenic preparation is possible with the process according to the invention without bringing the active ingredient into contact with reactive solvents or surfactants and without exposing it to light for a substantial time.

Besides gestogens, such as dienogest, additional active ingredients, especially hormones such as natural and/or synthetic antiandrogens(chlormadinon acetate), estrogens and corticoidal steroids, may be applied locally in a galenic preparation based on the above-described process. The pharmaceutical preparation thus made does not produce systemic effects or only produces slight systemic effects. The pharmaceutical preparations according to the invention with dienogest or a combination of dienogest and an estrogen and/or other natural and/or synthetic antiandrogens as active ingredient may be used for local treatment of a plurality of androgen caused maladies or diseases. Hair tonic, hair balm and/or hair cream based on the pharmaceutical preparation according to the invention can be used for treatment of hair loss or promotion of hair growth and as a palliative for and/or for elimination of vasomotor scalp pains. Thus, among other things, it is possible to prevent hair loss in women with androgen symptoms, especially in the post menopause phase, by direct application of the preparation according to the invention to the scalp skin, and/or to promote hair growth.

The invention will now be illustrated with the following examples, whose details should not be construed as limiting the appended claims.

EXAMPLES

| Example 1: Facial Lotion Solution | | |
| --- | --- | --- |
| 0.25 | g | dienogest |
| 0.40 | g | castor oil |
| 0.60 | g | benzyl benzoate |
| ad 100.0 | g | ethanol(96%) |
| q.s. | | dye compound, perfumes |
| 100.00 | g | |

Preparation:

Dienogest and benzyl benzoate are dissolved in a given amount of ethanol (96%). The mixture is heated briefly to 50° C. After that the mixture must be rapidly cooled to 20° C. Subsequently the required dyes and perfume materials dissolved in the given quantity of castor oil are added to the solution.

| Example 2: Facial Lotion Solution | | |
| --- | --- | --- |
| 0.25 | g | dienogest |
| 0.40 | g | peanut oil |
| 2.5 | g | lecithin |
| 2.0 | g | isopropyl myristate |
| ad 100.0 | g | ethanol(96%) |
| q.s. | | dye compound, perfumes |
| 100.00 | g | |

Preparation:

Dienogest and isopropyl myristate are dissolved in the given amount of 96% ethanol. Thus the mixture is briefly heated to 50° C. Subsequently it is rapidly cooled to 20° C. Finally the required dyes and aromatic materials which are previously dissolved with lecithin in the peanut oil, are added as a mixture with the oil and lecithin to the solution.

| Example 3: Skin Cream | | |
| --- | --- | --- |
| Part A | | |
| 4.5 | g | Bees wax |
| 9.5 | g | hard wax |
| 3.5 | g | lanolin |
| 8.0 | g | isopropyl myristate |

-continued

| Example 3: Skin Cream | | |
|---|---|---|
| 8.0 | g | liquid wax |
| 4.0 | g | glycerol |
| 37.5 | g | total for part A |
| Part B | | |
| 2.2 | g | dienogest |
| 4.4 | g | sacchrose |
| 6.6 | g | total for part B |
| Part C | | |
| 55.6 | g | deionized water |
| 0.2 | g | sodium tetraborate |
| 1.5 | g | boric acid |
| 0.7 | g | lactic acid |
| 62.2 | g | total for part C |
| Part D | | |
| q.s. | | preservative materials and perfumes. |

Preparation:

The materials of part A are heated to 90° C., melted and mixed. A solid dispersion (part B) made according to the method already described from dienogest and saccharose 1:2 is homogeneously dispersed in the melt. This is processed in the above-described reactor vessel according to the invention with the following conditions:

| | |
|---|---|
| vessel temperature after adding the solid dispersion: | 40° C. |
| rotation speed of the wiper | 1 rpm |
| rotation speed of the slower stirrer | 50 rpm |
| rotation speed of the homogenizer | 3450 rpm |
| cooling rate | 1° C./min |

| Example 4: Skin Salve | | |
|---|---|---|
| Part A | | |
| 4.0 | g | Bees wax |
| 9.5 | g | glycerol monostearate |
| 4.0 | g | lanolin |
| 8.0 | g | isopropyl myristate |
| 8.0 | g | paraffin(viscous liquid) |
| 4.0 | g | propylene glycol |
| 37.5 | g | total for part A |
| Part B | | |
| 20.0 | g | deionized water |
| 0.2 | g | sodium tetraborate |
| 20.2 | g | total for part B |
| Part C | | |
| 0.16 | g | dienogest |
| 19.84 | g | ethanol |
| 20.00 | g | total for part C |
| Part D | | |
| q.s. | | preservative materials and perfumes. |

Preparation:

The A portion was heated to 90° C., melted and mixed. The melt is mixed(partially saponified) with the borax solution which was also first heated to 90° C. Subsequently the mixture of parts A and B is cooled to below 50° C., before the ethanolic dienogest solution(part C) is mixed with it. Finally the preservative and perfume containing part D is added to the mixture of parts A, B and C. Then the product is cooled at 20° C. with stirring.

| Example 5: Skin Lotion | | |
|---|---|---|
| Part A | | |
| 0.50 | kg | dienogest |
| 9.45 | kg | ethanol |
| 0.05 | kg | glycerol |
| 10.00 | kg | |
| Part B | | |
| 1.0 | kg | sorbitan monostearate |
| 1.5 | kg | macrogol stearate |
| 2.5 | kg | medium chain length triglyceride |
| 0.05 | kg | potassium sorbate |
| 0.025 | kg | water-free citric acid water |
| ad 40.00 | kg | |

Preparation:

The solution(part A) is homogeneously distributed in the mixture B. The preparation then proceeds according to the general method described hereinabove with the following conditions:

| | |
|---|---|
| Vessel temperature on addition of solution A: | 30° C. |
| Rotation speed of the wiper: | 1 rpm |
| Rotation speed of the slower stirrer: | 90 rpm |
| Rotation speed of the homogenizer | 3850 rpm |
| Cooling rate: | 1° C. |

| Example 6: Lipogel | | |
|---|---|---|
| 5.0 | g | dienogest |
| 1000.0 | g | wool wax alcohol salve |

Preparation:

The micronized dienogest is uniformly distributed in the stated amount in the wool wax alcohol salve.

| Example 7: Lipogel + H with Dienogest | | |
|---|---|---|
| 5.0 | g | dienogest |
| 45.0 | g | lactose |
| | | wool wax alcohol salve to |
| 1000.0 | g | |

Preparation:

A solid dispersion of dienogest and lactose 1:9 is first prepared according to the above-described methods. This solid dispersion is uniformly distributed in the wool wax alcohol salve according to DAB 10. In an analogous smaller vessel, as described earlier in the description above, this is processed under the following conditions:

| | |
|---|---|
| vessel temperature after adding the solid dispersion: | 40° C. |
| rotation speed of the wiper | 2 rpm |
| rotation speed of the slower stirrer | 10 rpm |
| rotation speed of the homogenizer | 2050 rpm |
| cooling rate | 1° C./min |

Example 8: Hydrogel with Dienogest

| | | |
|---|---|---|
| 5.0 | g | dienogest |
| 400.0 | g | ethanol |
| 30.0 | g | methylhydroxyethyl cellulose |
| | | pure water to |
| 1000.0 | g | |

Preparation:

The stated amount of dienogest is dissolved in the ethanol and uniformly mixed with the aqueous methylhydroxyethyl cellulose gel as described above.

Example 9: Hydrogel with Dienogest and 17α-Estradiol

| | | |
|---|---|---|
| 5.0 | g | dienogest |
| 5.0 | mg | 17α-estradiol |
| 400.0 | g | ethanol |
| 30.0 | g | methylhydroxyethyl cellulose |
| | | pure water to |
| 1000.0 | g | |

Preparation:

The stated amounts of dienogest and 17α-estradiol are dissolved in ethanol and uniformly mixed with the aqueous methylhydroxyethyl cellulose gel as described above.

Example 10: Lipogel: Dienogest plus Estriol

| | | |
|---|---|---|
| 5.0 | g | dienogest |
| 20.0 | mg | estriol |
| | | wool wax alcohol salve to |
| 1000.0 | g | |

Preparation:

The dienogest and estriol are uniformly mixed in the stated amount in the wool wax alcohol salve.

Example 11: Hair Tonic or Hair Spray

| | | |
|---|---|---|
| 0.2 | g | dienogest |
| 0.4 | g | castor oil |
| 0.6 | g | benzyl benzoate |
| q.s. | | Dye compounds, perfumes |
| | | ethanol 96% ad |
| 100.0 | g | |

Preparation:

Dienogest and benzylbenzoate or isopropyl myristate are dissolved in the stated amount of ethanol. The mixture is briefly heated at 50° C. After that it is rapidly cooled to 20° C. Finally the required dye compounds and perfumes dissolved in the stated amount of castor oil are added to the resulting solution.

Example 12: Hair Tonic or Hair Spray

| | | |
|---|---|---|
| 0.2 | g | chlormadinon acetate |
| 0.4 | g | peanut oil |
| 2.5 | g | lecithin |
| 0.6 | g | benzylbenzoate |
| q.s. | | dye compounds, perfumes |
| | | ethanol 96% ad |
| 100.0 | g | |

Preparation:

The chlormadinon acetate and benzylbenzoate are dissolved in the stated amount of ethanol. Then the mixture is briefly heated at 50° C. After that it is rapidly cooled to 20° C. Finally the required dye compounds and perfumes dissolved in the stated amount of peanut oil are added to the resulting solution.

Example 13: Dienogest-Hair Balm with Hair-fixing Action (Conditioner)

Part A

| | | |
|---|---|---|
| 2.0 | g | cetyl lactate |
| 2.0 | g | isopropyl myristate |
| 4.0 | g | glycerol monostearate |
| 1.0 | g | polyethyleneglycol (PEG)-40-stearate |
| 2.0 | g | cetyl stearyl alcohol |
| 1.0 | g | cetyl alcohol |
| 12.0 | g | total |

Part B

| | | |
|---|---|---|
| 30.0 | g | aloe vera as colorless gel |
| 33.9 | g | deionized water |
| 0.3 | g | hydroxypropylmethyl cellulose(HPMC) |
| 3.4 | g | Quat's mixture of Quat-22 and Quat-26(2:5) |
| 0.3 | g | lactic acid |
| 67.9 | g | total |

Part C

| | | |
|---|---|---|
| 0.23 | g | dienogest |
| 19.75 | g | ethanol |
| 19.98 | g | total |

Part D

| | | |
|---|---|---|
| q.s. | | Dye compounds, preservatives and perfumes |

Preparation:

A glutinous mixture is made from the HPMC and water. The ingredients of Part B are added to the glutinous mixture. The resultant mixture is homogenized and after that heated to 80° C.(water bath). Part B is prepared by mixing the above-stated ingredients of it at 80° C.(water bath). Part B is then mixed with the same heating with Part A. The mixture of parts A and B is cooled with stirring at 50° C. The ethanolic solution (Part C) is added with stirring to the mixture of parts A and B cooled below 50° C. The resultant mixture is cooled further. Finally the required dye compounds, preservatives and perfumes are added to the mixture of parts A, B and C. The resultant mixture I then cooled with stirring to 20° C.

Example 14: Chlormadinon Acetate Hair Cream(Grooming Cream)

Part A

| | | |
|---|---|---|
| 4.0 | g | bees wax |
| 10.0 | g | glycerol monostearate |
| 3.5 | g | lanolin |
| 8.0 | g | isopropyl myristate |
| 8.0 | g | viscous paraffin |
| 4.0 | g | propylene glycol |
| 37.5 | g | total |

Part B

| | | |
|---|---|---|
| 20.0 | g | deionized water |
| 0.2 | g | sodium tetraborate |
| 20.2 | g | total |

-continued

Example 14: Chlormadinon Acetate Hair Cream(Grooming Cream)

Part C

| 0.19 g | chlomadinon acetate |
|---|---|
| 19.81 g | ethanol |
| 20.00 g | total |

Part D

| q.s. | Dye compounds, preservatives and perfumes |
|---|---|

Preparation:

The substances of Part A are heated at 90° C., then melted and mixed. The melt is mixed(partially saponified) with the borax solution(Part C) also heated at 90° C. The resultant mixture is subsequently cooled with stirring to under 50° C., before the ethanolic chlormadinon acetate solution (Part C) is added. Finally, the required dye compounds, preservatives and perfumes of Part D are added to the resulting mixture of parts A, B and C and the resulting mixture is cooled at 20° C. with stirring.

Example 15: Dienogest Hair Cream

Part A

| 4.0 g | bees wax |
|---|---|
| 10.0 g | hard wax |
| 3.5 g | lanolin |
| 8.0 g | isopropyl myristate |
| 8.0 g | liquid wax |
| 4.0 g | glycerol |
| 37.5 g | total |

Part B

| 0.2 g | dienogest(micronized) |
|---|---|

Part C

| 60.0 g | deionized water |
|---|---|
| 0.2 g | sodium tetraborate |
| 1.5 g | boric acid |
| 0.7 g | lactic acid |
| 62.4 g | total |

Part D

| q.s. | Dye compounds, preservatives and perfumes |
|---|---|

Preparation:

The ingredients of Part A are heated at 90° C., then melted and mixed. The micronized dienogest (Part B), protected from light, is mixed in this melt. The resultant mixture is subsequently cooled with stirring to under 50° C. The water phase C is added with stirring to the cooled mixture of parts A and B. The resulting mixture is cooled further below 50° C. Finally, the required dye compounds, preservatives and perfumes of Part D are added to the resulting mixture of parts A, B and C and the resulting mixture is cooled at 20° C. with stirring.

The purpose of these pharmaceutical preparations, above all, is the penetration of the active ingredient into the skin while limiting or preventing resorption and the penetration of the active ingredient through the skin.

Clinical Tests

To test the performance of the formulae or compositions of the above-described examples, portions of hydrogel (Hydrogel, Example 8) and a Lipogel without (Lipogel, Example 6) and with a hydrophilic additive according to the invention (Lipogel+H., Example 7) were applied to three human test subjects respectively under the following conditions: application amount, 2 g(10 mg dienogest); surface, forehead; and acting time 3 h.

Figure 4:
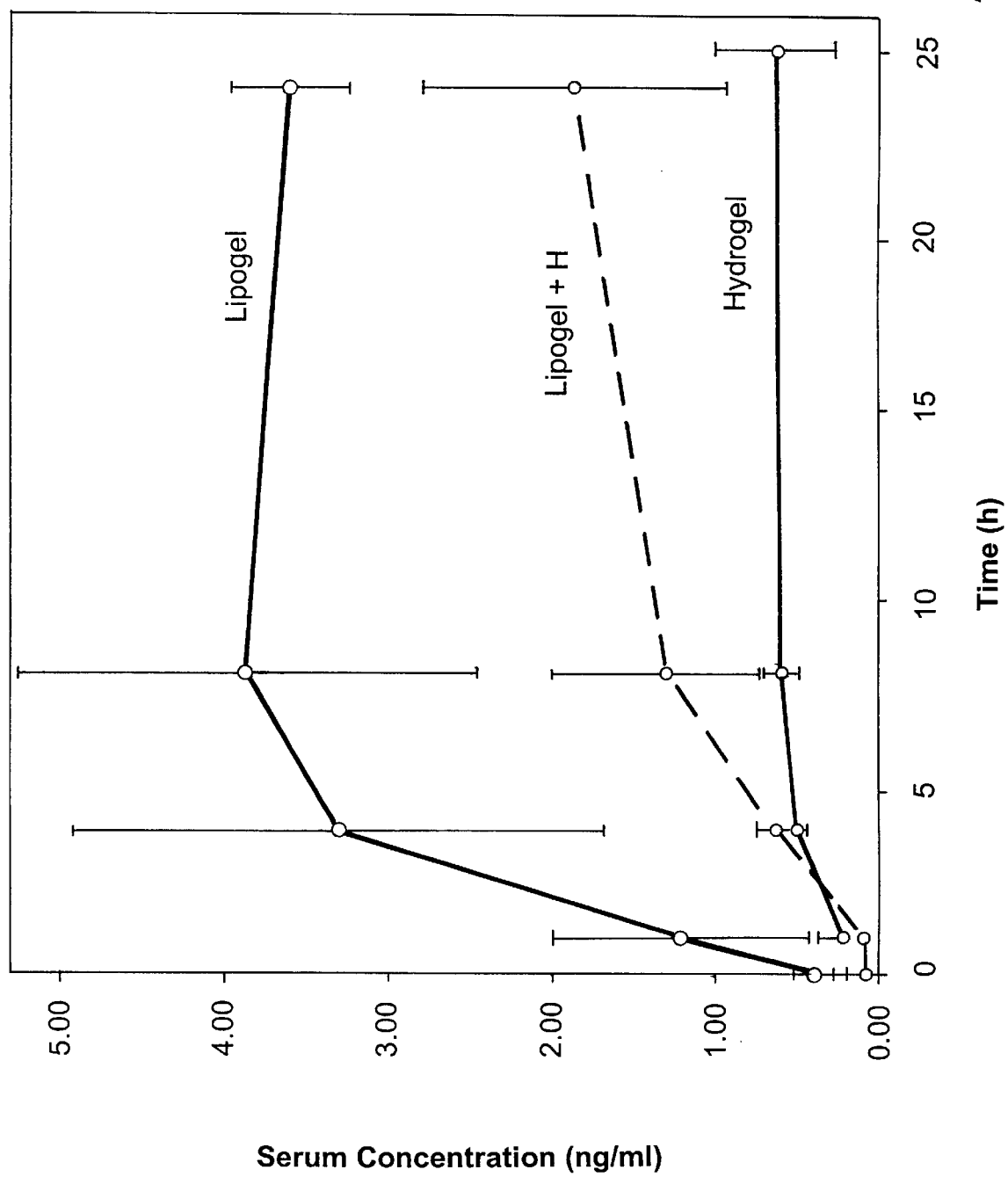
FIG. 4 is a graphical illustration comparing dienogest concentration-time curves in serum for different preparations according to the invention.

After that the dienogest serum level was determined by means of RIA. As shown in FIG. 4 while a comparatively large amount of dienogest is found in the serum from a pharmaceutically ordinary lipogel, this is not the situation when the hydrogel and the lipogel with hydrophilic additive are used. The serum level of both the latter preparations does not differ significantly from each other. Both serum levels of these preparations differ significantly from the serum level of dienogest resulting from application of the lipogel without the additional additive. That means that with these latter preparations significantly more dienogest remains in the skin and as a result systemic side effects are largely prevented. The serum concentration of dienogest usually required for systemic side effects amounts to 40 to 50 ng/ml. The dienogest serum level after application of the preparation according to the invention amounts to about a factor of 20 lower than this threshold for side effects.

All forms of acne and increased sebum production (seborrhea) are treatable by topical application of the dienogest-containing formulations(facial lotions, skin salves, skin creams, lotions). The sebaceous gland activity has a typical time course in women during aging. Approximately every second women, beginning with the age of puberty, has a more or less remarkably increased sebaceous gland secretion which can lead to oily skin.

In a study of penetration by dienogest of intact skin in 9 human test subjects it was proven that the effective ingredient (hydrogel formulation) did not penetration into the body. No active ingredients were found in the blood plasma of 5 acne patients 12 and 24 hours after being treated twice with the compositions according to the invention (10 mg dienogest in 2 g skin salve).

The effect of a 2.2 g dienogest-containing skin cream (example 2) was tested in acne patients and patients with seborrhea during activity studies in 24 women of ages between 18 and 45 years and 18 men of ages between 24 and 46 years. In all patients the dienogest-containing skin cream was applied to the right half of the forehead. The left half of the forehead acted as control. The skin cream was applied twice daily(morning and evening) to the skin area to be treated. The experiment duration was 8 weeks. In all patients a considerable reduction of the sebum generation was observed already after 8 treatment days. A remarkable reduction of skin surface lipids of about 42 to 47% was observed in both male and female test subjects after 14 to 21 days. Particularly a decline of the wax components was observed. These waxes are of greater significance in the production of acne and comedones. A definite improvement in the acne conditions present in the patients was observed in 4 to 8 weeks of treatment. In 52% of the acne patients after 4 treatment weeks no symptoms remained. After 8 weeks of therapy only 12% of the acne patients had any noticeable acne present and in these cases exceptionally pronounced acne had been present at the start of the treatment. Also in these patients a clearly positive course of the treatment was observed during the eight weeks of treatment.

The dienogest-containing preparations (facial lotion, skin salve, skin cream, lotion) according to the invention are used so that the increased sebaceous gland secretions(seborrhea) and the noninflammed acne are successfully prevented with the help of a sufficient amount of the respective preparations. It is recommended that the topical formulation be used on the skin with various concentrations according to the individual case depending on the strength of the disease being treated. Prior to the beginning of therapy of androgenic conditions skin changes a determined of the individual hormone status is recommended in fertile females.

The treatment with the dienogest-containing skin agent extends to the diseased portions of the skin(seborrhea, acne areas, alopecia, androgenizing symptoms in women). It is recommended that daily applications or applications several times a day be made during treatment of these skin diseases.

Clinical Tests of Acne and Seborrhea Treatments

The tests 1 to 5 hereinbelow exemplify the application of the compositions according to the invention for the treatment of acne and seborrhea.

Test 1

A 0.25% dienogest-containing facial lotion was used for treatment of seborrhea. With increased sebaceous gland production a twice daily application to the affected areas is recommended with increased sebaceous gland production in the facial area. This hormonal agent was used over a period of eight weeks and provided an outstanding sebum suppression.

Test 2

For acne therapy a 3% dienogest-containing skin cream was applied twice daily to the skin areas infected with acne in an acne therapy program. The cream was applied over a 3 month test interval and a very good therapeutic action was observed already after 4 treatment weeks in sever cases of acne.

Test 3

A 0.2% dienogest-containing skin salve was applied at least once per day for treatment of excessive sebum production of the sebaceous gland in the skin. Within a few minutes the salve was absorbed by the skin. The performance observed was similar to the outstanding performance observed during test 1.

Test 4

An 0.5% dienogest-containing lotion was used a preparation for acne therapy. The lotion was applied to the areas having acne twice daily. A very good therapeutic action was observed for this preparation because of the rapid penetration into the skin. The results were similar to those of test 2.

Test 5

An 0.5% dienogest-containing hydrogel which contained 5 mg of 17α-estradiol in 1000 g gel, was applied for treatment of acne. The gel was applied once a day for a 3 month test period. Already after 4 treatment weeks a definite sebosuppression effect was observed with partial eliminated of comedones.

The following tests 6 to 8 shows the application of the compositions according to the invention for the treatment of hair loss and the promotion of hair waxes.

Test 6

For treatment of the entire scalp skin use of a 0.2% hair tonic/hair spray is recommended, in which a total dose of 20 ml per week should not be exceeded.

Test 7

A 0.5% hair tonic/spray is recommended for treatment of postmenopausal androgenically conditioned hair loss at a maximum dosage up to 20 ml per week.

Test 8

For a locally limited androgenically conditioned hair loss only the scalp region (peaks areas, forehead surfaces, rear scalp surfaces)involved should be treated with balm and/or hair cream or hair spray daily or at least 3 times in one week.

A successful therapeutic result in the form of increased hair growth was observed in tests 6 to 8 after 3 treatment months.

The invention described and claimed herein is also described in German Patent Application 195 34 209.7-41 filed in Germany on Sep. 16, 1995. Priority rights based on the aforesaid German Patent Application are being claimed. The disclosure in the priority document, German Patent Application 195 34 209.7-41, is incorporated in this specification by reference.

While the invention has been illustrated and described as embodied in a pharmaceutical composition including a hormonal agent and method for skin treatment, especially of seborrhea, acne and the like, and a method of making the pharmaceutical composition, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims: What is claimed is:

1. A method of treating skin with seborrhea, said method consisting of applying an effective amount of a pharmaceutical preparation to local areas of said skin containing said seborrhea, wherein said pharmaceutical preparation contains dienogest or a combination of dienogest and an estrogen as an active ingredient for treating said skin with said seborrhea, wherein said estrogen is selected from the group consisting of 17α-estradiol and estriol.

2. The method as defined in claim 1, wherein said pharmaceutical preparation is in the form of a facial lotion, a skin salve, a skin cream or a lotion, said applying of said pharmaceutical preparation occurs at least once a day during the treating and said pharmaceutical preparation is allowed to penetrate said local areas of said skin.

3. A method of treating skin with seborrhea and/or acne, said method consisting of applying an effective amount of a pharmaceutical preparation to local areas of said skin containing said seborrhea and/or acne, wherein said pharmaceutical preparation contains dienogest or a combination of dienogest and an estrogen as an active ingredient for treating said skin with said seborrhea and/or acne.

4. A method of treating skin with seborrhea and/or acne, said method consisting of applying an effective amount of a pharmaceutical preparation to areas of said skin containing said seborrhea and/or acne, wherein said pharmaceutical preparation contains from 0.01 to 4% by weight of dienogest.

5. The method as defined in claim 4, wherein said pharmaceutical preparation contains an estrogen in addition to said dienogest.

6. The method as defined in claim 4, wherein said pharmaceutical preparation contains, in addition to said dienogest, an estrogen member selected from the group consisting of 17α-estradiol and estriol.

7. A method of treating skin with *Acne vulgaris*, said method consisting of applying an effective amount of a pharmaceutical preparation to local areas of said skin containing said *Acne vulgaris*, wherein said pharmaceutical preparation contains dienogest or a combination of dienogest and an estrogen as an active ingredient for treating said skin with said *Acne vulgaris*, wherein said estrogen is selected from the group consisting of 17α-estradiol and estriol.

8. The method as defined in claim 7, wherein said pharmaceutical preparation is in the form of a facial lotion, a skin salve, a skin cream or a lotion, said applying of said pharmaceutical preparation occurs at least once a day during the treating and said pharmaceutical preparation is allowed to penetrate said local areas of said skin.

9. A skin cream or salve for treating skin with seborrhea and/or acne, said skin cream or salve consisting of from 0.01 to 4% by weight of dienogest in a deoiling foundation.

10. The skin cream or salve as defined in claim 9, containing wool wax alcohol salve and in the form of a lipogel.

11. A skin cream or salve for treating skin with seborrhea and/or acne, said skin cream or salve consisting of an estrogen selected from the group consisting of estriol and 17α-estradiol and from 0.01 to 4% by weight of dienogest in a deoiling foundation.

12. The skin cream or salve as defined in claim 11, containing wool wax alcohol salve and in the form of a lipogel.

13. A composition for treating skin with seborrhea and/or acne, said composition containing from 0.01 to 4% by weight of dienogest and an amount of wax and/or oil sufficient to form a cream or salve.

14. A composition for treating skin with seborrhea and/or acne, said composition containing at least one estrogen selected from the group consisting of estriol and 17α-estradiol, from 0.01 to 4% by weight of dienogest and an amount of wax and/or oil sufficient to form a cream or salve.

15. A skin lotion for treating skin with seborrhea and/or acne, said skin lotion consisting of at least one estrogen selected from the group consisting of estriol and 17α-estradiol and from 0.01 to 4% by weight of dienogest in a hydrophilic foundation, said hydrophilic foundation comprising ethanol and at least one other member selected from the group consisting of water, glycerol and propylene glycol.

16. A skin lotion for treating skin with seborrhea and/or acne, said skin lotion consisting of from 0.01 to 4% by weight of dienogest in a hydrophilic foundation, said hydrophilic foundation containing ethanol and at least one other member selected from the group consisting of water, glycerol and propylene glycol.

* * * * *